(12) United States Patent
Montel et al.

(10) Patent No.: US 9,630,948 B2
(45) Date of Patent: Apr. 25, 2017

(54) COMPOUNDS FOR ENHANCING THE COGNITIVE FUNCTION

(71) Applicant: UCB Pharma, S.A., Brussels (BE)

(72) Inventors: Florian Montel, Biberach an d. Riss (DE); Eric Jnoff, Ecaussinnes (BE)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 14/909,246

(22) PCT Filed: Jul. 28, 2014

(86) PCT No.: PCT/EP2014/066159
§ 371 (c)(1),
(2) Date: Feb. 1, 2016

(87) PCT Pub. No.: WO2015/014785
PCT Pub. Date: Feb. 5, 2015

(65) Prior Publication Data
US 2016/0185761 A1    Jun. 30, 2016

(30) Foreign Application Priority Data
Aug. 2, 2013  (EP) ..................... 13179148

(51) Int. Cl.
*A01N 43/64*    (2006.01)
*A61K 31/41*    (2006.01)
*C07D 249/08*   (2006.01)
*C07D 403/06*   (2006.01)

(52) U.S. Cl.
CPC ................. *C07D 403/06* (2013.01)

(58) Field of Classification Search
None
See application file for complete search history.

(56) References Cited

FOREIGN PATENT DOCUMENTS

| WO | 2006/128692 A2 | 12/2006 | |
|----|----|----|----|
| WO | WO 2006128692 A2 * | 12/2006 | ........... C07D 401/06 |
| WO | 2011/015349 A2 | 2/2011 | |

* cited by examiner

*Primary Examiner* — Dennis Heyer
*Assistant Examiner* — Daniel M Podgorski
(74) *Attorney, Agent, or Firm* — McDonnell Boehnen Hulbert & Berghoff LLP

(57) ABSTRACT

The invention relates to 2-oxo-1-pyrrolidinyl triazole derivatives, processes for preparing them, pharmaceutical compositions containing them and their use as pharmaceuticals for enhancing the cognitive function or to counteract cognitive decline.

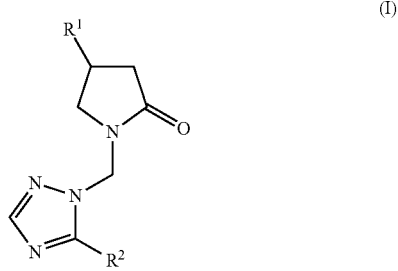

(I)

17 Claims, No Drawings

COMPOUNDS FOR ENHANCING THE COGNITIVE FUNCTION

This application is a US national phase of International Application No. PCT/EP2014/066159 filed on Jul. 28, 2014, which claims priority to European Patent Application No. 13179148.5 filed on Aug. 2, 2013.

FIELD OF THE INVENTION

The invention relates to 2-oxo-1-pyrrolidinyl triazole derivatives, processes for preparing them, pharmaceutical compositions containing them and their use as pharmaceuticals for enhancing the cognitive function or to counteract cognitive decline in a mammal.

BACKGROUND OF THE INVENTION

Cognitive disorders, i.e. impairments of memory and learning processes, have a significant detrimental effect on the quality of life of patients affected by it. Clinically recognized cognitive disorders vary from mild cognitive impairment through to dementia of varying severity. Cognitive disorders may also be associated with several disease or disorders such as schizophrenia, depression or Parkinson's disease.

Mild cognitive impairment ("MCI") is believed to be a transition stage between the cognitive changes of normal aging and the more serious problems caused by Alzheimer's disease. Dementia is a clinically recognized broad-spectrum syndrome entailing progressive loss of cognitive capabilities. Dementia can be one of many symptoms of various neurological diseases or the main abnormality associated with the disease, as it is the case in Alzheimer's disease. Most common causes of dementia include cerebral atrophy associated with Alzheimer's disease, Lewy-bodies disease, front-temporal lobe degeneration, Pick's disease, vascular narrowing or blockage in the brain (i.e. vascular dementia also known as multi-infarct dementia), Huntington's disease, Parkinson's disease, head trauma, HIV infection or Down's syndrome.

Alzheimer's disease (AD) is a progressive degenerative disease of the brain primarily associated with aging. AD is one of several disorders that cause the gradual loss of brain cells and is one of and possibly the leading cause of dementia. Clinical presentation of AD is characterized by loss of memory, cognition, reasoning, judgment, and orientation. Mild cognitive impairment (MCI) is often the first identified stage of AD. As the disease progresses, motor, sensory, and linguistic abilities also are affected until there is global impairment of multiple cognitive functions. These cognitive losses occur gradually, but typically lead to severe impairment, and the disease leads eventually to death in the range of three to twenty years.

Currently there are only a few medications that have been shown to afford at most a modest, mostly transient benefit to the patients suffering from cognitive impairment. Cholinesterase inhibitors (anticholinesterases), such as donepezil (Aricept®), galanthamine (Razadyne®, Razadyne ER®, Reminyl®, Nivalin®) and rivastigmine tartrate (Exelon®) have been shown to be efficacious in mild to moderate Alzheimer's disease dementia. Exelon® has recently been approved for the treatment of mild to moderate dementia associated with Parkinson's disease. Memantine, a NMDA receptor antagonist, is the first approved Alzheimer's disease medication acting on the glutamatergic system (Axura®, Akatinol®, Namenda®, Ebixa®). These drugs however have not only proven limited efficacy but also considerable side effects which in some cases lead to discontinuation of the therapy. With the increase in the life span and general aging of the population there is a need to develop drugs which could delay or alleviate the cognitive function in aging patients.

Cognitive impairment associated with schizophrenia (CIAS) is an intrinsic part of the illness, affecting the majority of the patients, and often pre-dates its onset. It affects a wide range of cognitive functions, particularly memory, attention, motor skills, executive function and social cognition following dysregulation of several neurotransmitter systems. No treatment are currently specifically approved for CIAS (O'Carroll, Advances in Psychiatric Treatment 6, 161-168 (2000); Millan et al., Nature Rev. Drug Discovery 11, 141-168 (2012)).

Levetiracetam or (S)-(−)-alpha-ethyl-2-oxo-1-pyrrolidine acetamide, is a laevorotatory compound, disclosed in the European patent No. EP-162036 as being a protective agent for the treatment and the prevention of hypoxic and ischemic type aggressions of the central nervous system. Levetiracetam has the following structure:

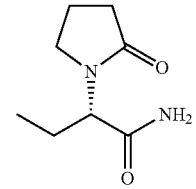

Levetiracetam has been approved, and is marketed as Keppra®, in many countries including the European Union and the United States for the treatment of various forms of epilepsy, a therapeutic indication for which it has been demonstrated that its dextrorotatory enantiomer (R)-(+)-alpha-ethyl-2-oxo-1-pyrrolidine acetamide completely lacks activity (Gower et al., Eur. J. Pharmacol. 222, 193-203 (1992)).

It has been repeatedly reported however that levetiracetam has no impact on the cognitive function both in animals as well as in humans (Lamberty et al, Epilepsy & Behavior 1, 333-342 (2000); Klitgaard et al. Epilepsy Research 50, 55-65 (2002); Shannon H & Love, P. Epilepsy & Behavior 7, 620-628 (2005); Higgins et al. Psychopharmacology 207, 513-527 (2010)).

Further racetam-type drugs include piracetam, oxiracetam, aniracetam, pramiracetam and phenylpiracetam, which have been used in humans and some of which are available as dietary supplements. Of these, oxiracetam and aniracetam are no longer in clinical use. Pramiracetam reportedly improved cognitive deficits associated with traumatic brain injuries. Although piracetam exhibited no long-term benefits for the treatment of mild cognitive impairments, recent studies demonstrated its neuroprotective effect when used during coronary bypass surgery. It was also effective in the treatment of cognitive disorders of cerebrovascular and traumatic origins; however, its overall effect on lowering depression and anxiety was higher than improving memory. As add-on therapy, it appears to benefit individuals with myoclonus epilepsy and tardive dyskinesia. Phenylpiracetam is more potent than piracetam and is used for a wider range of indications. In combination with a vasodilator drug, piracetam appeared to have an additive beneficial effect on various cognitive disabilities.

Pyrrolidone derivatives in particular for the treatment of epilepsy are disclosed in WO 2006/128693:

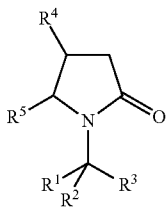

In said formula
R³ may be—among others—a 1H-1,2,4-triazol-1-yl and R⁴ may be a substituted or unsubstituted aryl.

One specific triazole pyrrolidone compound having the following formula is disclosed in WO 2006/128693

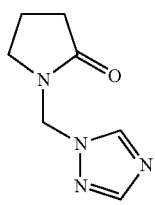 [SMILES: O=C1CCCN1Cn1cncn1]

SUMMARY OF THE INVENTION

The present invention relates to compounds, compositions and methods for the treatment of conditions associated with enhancement or improvement of cognitive ability or to counteract cognitive decline.

A further aspect of the present invention consists in pharmaceutical compositions containing a compound which has been identified pursuant to the above set out method and which may furthermore contain a pharmaceutically acceptable excipient.

Further aspects of the invention will become apparent from the detailed specification.

DETAILED DESCRIPTION OF THE INVENTION

The compounds and their tautomers, isomers and salts useful for the treatment of conditions associated with enhancement or improvement of cognitive ability or to counteract cognitive decline are of those of formula (I)

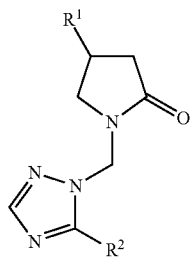

(I)

wherein
R¹ is a 3,4,5-trifluorophenyl or a 3-cyanophenyl moiety;
R² is either a cyano moiety of formula —CN or a chlorine atom.

In one embodiment the R¹ group of formula (I) is in the 4R configuration. In another, it is in the 4S configuration.

In a preferred embodiment the R¹ group is a 3,4,5-trifluorophenyl moiety.

Specific compounds of the present invention are those selected from the group consisting of:
(4R)-1-[(5-chloro-1H-1,2,4-triazol-1-yl)methyl]-4-(3,4,5-trifluorophenyl)pyrrolidin-2-one;
1-{[(4R)-2-oxo-4-(3,4,5-trifluorophenyl)pyrrolidin-1-yl]methyl}-1H-1,2,4-triazole-5-carbonitrile;
(+)-3-{1-[(5-chloro-1H-1,2,4-triazol-1-yl)methyl]-5-oxopyrrolidin-3-yl}benzonitrile.

The compounds of formula (I) according to the invention can be prepared analogously to conventional methods as understood by the person skilled in the art of synthetic organic chemistry.

According to one embodiment, compounds having the general formula I may be prepared by nucleophilic substitution of a compound of formula II by a triazole of formula III according to the equation:

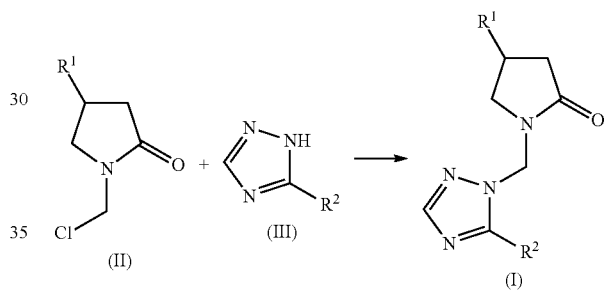

wherein R¹ and R² have the same definitions as defined above for compounds of formula I.

This reaction may be performed for example in tetrahydrofurane or in toluene in the presence of a base such as sodium hydride, or according to any method known to the person skilled in the art.

Compounds of formula II may be prepared by chlorination of a compound of formula IV, or according to any method known to the person skilled in the art.

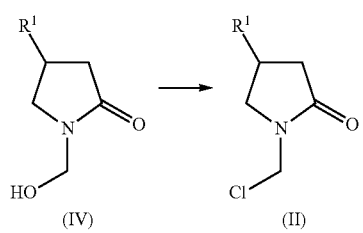

wherein R¹ has the same definitions as defined above.

This reaction may be performed for example in dichloromethane at 0° C. in the presence of oxalyl chloride, or according to any method known to the person skilled in the art.

Compounds of formula IV may be prepared by formylation of a pyrrolidone of formula V according to the equation:

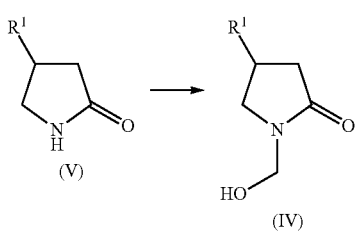

wherein R¹ has the same definitions as defined above.

This reaction may be performed for example in tetrahydrofurane at room temperature in the presence of paraformaldehyde and a base such as potassium tert-butoxide, or according to any method known to the person skilled in the art.

Compounds of formula V may be prepared by deprotection of a compound of formula VI according to the equation:

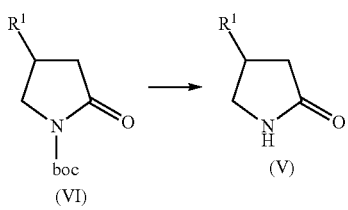

wherein R¹ has the same definitions as defined above.

This reaction may be performed for example at room temperature in dichloromethane in the presence of an acid such as trifluoroacetic acid, or according to any method known to the person skilled in the art.

The synthesis of compounds of formula VI can be performed using procedures described in the literature (for example in WO 2006/128693) or according to any method known to the person skilled in the art.

In another embodiment, the present invention includes the synthesis of the following intermediates:
(4R)-4-(3,4,5-trifluorophenyl)pyrrolidin-2-one;
(4R)-1-(hydroxymethyl)-4-(3,4,5-trifluorophenyl)pyrrolidin-2-one;
(4R)-1-(chloromethyl)-4-(3,4,5-trifluorophenyl)pyrrolidin-2-one;
tert-butyl 4-(3-cyanophenyl)-2-oxopyrrolidine-1-carboxylate;
3-(5-oxopyrrolidin-3-yl)benzonitrile;
3-[1-(hydroxymethyl)-5-oxopyrrolidin-3-yl]benzonitrile; and
3-[1-(chloromethyl)-5-oxopyrrolidin-3-yl]benzonitrile.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Compounds of formula I and some of their intermediates have at least one stereogenic center in their structure. This stereogenic center may be present in a R or a S configuration, said R and S notation is used in correspondence with the rules described in Pure Appl. Chem. 45, 11-30 (1976).

The invention also relates to all enantiomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

The expression "enantiomerically pure" as used herein refers to compounds which have enantiomeric excess (ee) greater than 95%.

Also included by formula (I) are those compounds where the predominant isotope of hydrogen is replaced by the deuterium or tritium.

Compounds according to the present invention may exist in different polymorphic forms. Although not explicitly indicated in the above formula, such forms are intended to be included within the scope of the present invention.

The compounds of the present invention are for use as a medicament, in the treatment of conditions associated with enhancement or improvement of cognitive ability or to counteract cognitive decline.

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 0.1 to 2000 mg, preferably 0.1 to 1000 mg, more preferably 0.1 to 500 mg of active ingredient per unit dosage form.

The terms "treatment of conditions associated with enhancement or improvement of cognitive ability" or "to counteract cognitive decline" or "treatment of a cognitive disorder" or "improving the cognitive function" or "counteracting the decline of the cognitive function" used throughout this specification shall mean promoting cognitive function (affecting impaired cognitive function in the subject so that it more closely resembles the function of an aged-matched normal, unimpaired subject, including affecting states in which cognitive function is reduced compared to a normal subject) and preserving cognitive function (affecting normal or impaired cognitive function such that it does not decline or does not fall below that observed in the subject upon first presentation or diagnosis, e.g. to the extent of expected decline in the absence of treatment). The suitability of the compounds according to the present invention for conditions associated with enhancement or improvement of cognitive ability may be tested through assays that are well known in the art. Such assays include in particular the novel object recognition tests set out in Example 4 and 5, as well as the Y-maze test set out in Example 6.

In one embodiment of the invention, the mammal has normal cognitive function which is improved.

In a further embodiment the mammal exhibits cognitive impairment associated with aging.

In still a further embodiment the mammal is a human with cognitive impairment associated with a disease or disorder such as autism, dyslexia, attention deficit hyperactivity disorder, compulsive disorders, psychosis, bipolar disorders, depression, Tourette's syndrome and disorders of learning in children, adolescents and adults, Age Associated Memory Impairment, Age Associated Cognitive Decline, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening.

In still a further embodiment, the impairment of cognitive function is caused by, or attributed to, Alzheimer's disease. In another embodiment, the impairment of cognitive function is caused by, or attributed to, mild cognitive impairment (MCI). In a further embodiment, the impairment of cognitive function is caused by, or attributed to, schizophrenia.

The compounds according to the present invention may be used for the manufacture of a pharmaceutical composition for the treatment of a cognitive disorder or for improving the cognitive function or counteracting the decline of the cognitive function. Such compositions typically contain the active pharmaceutical ingredient and a pharmaceutically acceptable excipient.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diaminetetraacetic acid, buffers such as acetates, citrates or phosphates and agents for adjusting the osmolarity, such as sodium chloride or dextrose.

Also comprised by the present invention are pharmaceutical compositions containing the compound of the present invention in the form of a pharmaceutically acceptable co-crystal.

Such pharmaceutical compositions may furthermore contain known or marketed therapeutic agents used in the treatment of cognitive or a neurological disorders (AD) including but not limited to donepezil (Aricept®), galanthamine (Razadyne®, Razadyne ER®, Reminyl®, Nivalin®), rivastigmine tartrate (Exelon®), memantine (Axura®, Akatinol®, Namenda®, Ebixa®).

The pro-cognitive activity of the compounds according to the present invention in particular of formula I, or their pharmaceutically acceptable salts, may be determined by a variety of preclinical tests and models known to a skilled person in the art. Such tests may challenge the efficacy on multiple memory phases and types. In contrast to challenging a particular memory type or phase, the cognitive models test the ability of a compound to prevent or reverse a memory deficit in a given brain pathway, system, or function.

In pre-clinical animal models, the compounds according to the present invention improve cholinergic memory deficit induced by scopolamine, a muscarinic receptor antagonist. They also improve the memory deficit induced by beta-amyloid or by subchronic administration of phencyclidine (PCP), a non-competitive NMDA antagonist. Memory deficits in Alzheimer's disease may have both a cholinergic origin as a consequence of specific cholinergic degeneration during disease progression, and an amyloid origin as a consequence of beta-amyloid increase in the brain. Cognitive deficits in schizophrenia result from dysregulation of several neurotransmitter systems, including glutamate and dopamine, mimicked by the effects of NMDA antagonists such as PCP. Therefore, it is believed that the compounds according to the present invention have a strong potential to improve cognitive deficits in Alzheimer's disease and cognitive impairment associated with schizophrenia.

Unexpectedly, the compounds according to the present invention display strong activities in in vivo models for cognition (see Examples 4, 5 and 6).

EXAMPLES

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

NMR spectra are recorded on a BRUKER AVANCE 400 NMR Spectrometer fitted with a Linux workstation running XWIN NMR 3.5 software and a 5 mm inverse 1H/BB probehead, or BRUKER DRX 400 NMR fitted with a SG Fuel running XWIN NMR 2.6 software and a 5 mm inverse geometry $^{1}H/^{13}C/^{19}F$ triple probehead. The compound is studied in d6-dimethylsulfoxide (or d3-chloroform) solution at a probe temperature of 313 K or 300 K and at a concentration of 10 mg/ml. The instrument is locked on the deuterium signal of $d_6$-dimethylsulfoxide (or $d_3$-chloroform). Chemical shifts are given in ppm downfield from TMS (tetramethylsilane) taken as internal standard.

Mass spectrometric measurements in LC/MS mode are performed as follows:

HPLC Conditions

Analyses are performed using a WATERS Alliance HPLC system mounted with an INERTSIL ODS 3, DP 5 μm, 250×4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures. Reverse phase separations are carried out using 500 g of either Kromasil C18 10 μm silicagel (acidic or neutral conditions) or Phenomenex Gemini C18 10 μM (basic conditions) in 8-cm ID columns with a flow rate of 150 ml/min. Products are detected at 215 nm unless otherwise specified.

Preparative Chiral Chromatographic separations are performed on a DAICEL Chiralpak IC 20 μm, 100*500 mm column using an in-house build instrument with various mixtures of lower alcohols and C5 to C8 linear, branched or cyclic alkanes at ±350 ml/min. Solvent mixtures as described in individual procedures.

Example 1

Synthesis of (4R)-1-[(5-chloro-1H-1,2,4-triazol-1-yl)methyl]-4-(3,4,5-trifluorophenyl)pyrrolidin-2-one 7

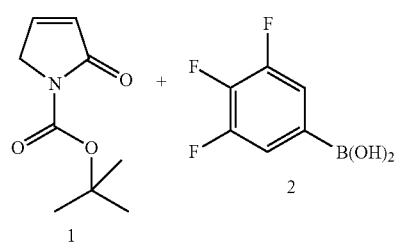

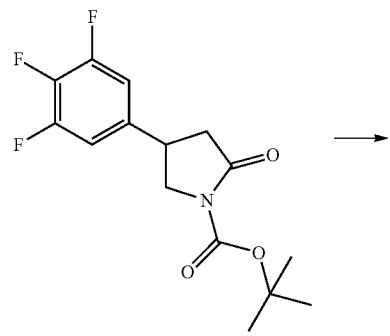

3
(+)-3A
(−)-3B

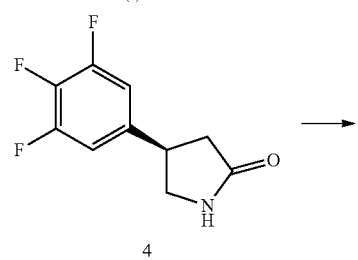

4

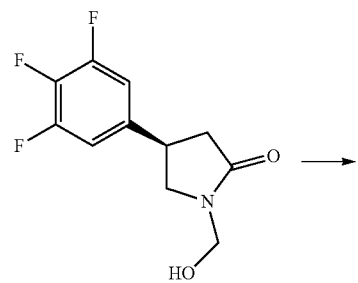

5

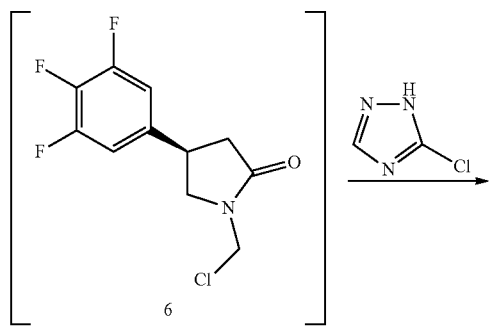

6

7

1.1 Synthesis of tert-butyl 2-oxo-4-(3,4,5-trifluoro-phenyl)pyrrolidine-1-carboxylate 3 and enantiomers To a solution of tert-butyl 2-oxo-2,5-dihydro-1H-pyrrole-1-carboxylate 1 (10 g, 1 eq., 54.6 mmol) in dioxane/water (100 ml/30 ml) are added at room temperature (3,4,5-trifluorophenyl)boronic acid 2 (19.2 g, 2 eq., 109.2 mmol), cesium fluoride (24.9 g, 3 eq., 163.8 mmol), (±)-2,2'-bis(diphenyl-phosphino)-1,1'-binaphthyl (1.5 g, 4.5%, 2.5 mmol), potassium carbonate (22.6 g, 3 eq., 163.8 mmol) and chloro(1,5-cyclooctadiene)rhodium(I)dimer (0.82 g, 1.5%, 8.2 mmol). The mixture is heated at 110° C. for 2 h. Solvent are removed under reduced pressure and the residue is purified by chromatography over silicagel (eluent: $CH_2Cl_2$/MeOH/$NH_4OH$ 96/3.5/0.5 v/v/v) to afford tert-butyl 2-oxo-4-(3,4,5-trifluorophenyl)pyrrolidine-1-carboxylate 3. The enantiomers are resolved by chiral chromatography (chiralpak IC, 150*4.6 mm, eluent: heptane/AcOEt/diethylamine 80/20/0.1 v/v/v) to afford tert-butyl (4R)-2-oxo-4-(3,4,5-trifluorophenyl)pyrrolidine-1-carboxylate 3A (second eluted, 5.1 g), and its enantiomer tert-butyl (4S)-2-oxo-4-(3,4,5-trifluorophenyl)pyrrolidine-1-carboxylate 3B (first eluted, 5.2 g) as white solids.

Compound 3A:
Yield: 30%.
LC-MS ($MH^+$): 316.
$alpha_D$ (MeOH, 25° C.): −19.9.

1.2 Synthesis of (4R)-4-(3,4,5-trifluorophenyl)pyrrolidin-2-one 4

At 0° C., TFA (20 ml, 261 mmol) is added to a solution of tert-butyl (4R)-2-oxo-4-(3,4,5-trifluorophenyl)pyrrolidine-1-carboxylate 3A (8 g, 1 eq., 25.4 mmol) in dichloromethane (100 ml). The mixture is stirred at room temperature for 2 h. Then, TFA and solvent are removed under reduced pressure. The crude mixture is poured in an aqueous saturated solution of $NaHCO_3$ (100 ml) and extracted with AcOEt (3*200 ml). The combined organic extracts are dried over $MgSO_4$ and concentrated under reduced pressure. The conversion is total and the evaporation affords 5.5 g of (4R)-4-(3,4,5-trifluorophenyl)pyrrolidin-2-one 4, which is used in the next step without any further purification.

LC-MS ($MH^+$): 216; LC-MS ($MH^-$): 214.
$alpha_D$ (MeOH, 22° C.): −20.1.

1.3 Synthesis of (4R)-1-(hydroxymethyl)-4-(3,4,5-trifluorophenyl)pyrrolidin-2-one 5

To a solution of (4R)-4-(3,4,5-trifluorophenyl)pyrrolidin-2-one 4 (5.5 g, 1 eq., 25.6 mmol) in THF (20 ml) are added potassium tert-butoxide (0.049 g, 0.02 eq., 0.44 mmol) and paraformaldehyde (0.95 g, 1.2 eq., 31.1 mmol) at room temperature. After overnight stirring at 60° C., the mixture is quenched with brine (100 ml) and the aqueous phase is extracted with AcOEt (2*100 ml). The combined organic extracts are dried over $MgSO_4$ and concentrated under reduced pressure yielding 4.7 g of (4R)-1-(hydroxymethyl)-4-(3,4,5-trifluorophenyl)pyrrolidin-2-one 5, which is used in the next step without any further purification.

LC-MS ($MH^+$): 246.
$^1$H NMR (DMSO) δ 7.34 (dd, $J_1$=9.2 Hz, $J_2$=6.8 Hz, 2H), 5.87 (t, J=6.8 Hz, 1H), 4.70 (m, 2H), 3.78 (m, 1H), 3.62 (m, 1H), 3.40 (m, 1H), 2.68 (m, 1H), 2.43 (dd, $J_1$=16.6 Hz, $J_2$=8.6 Hz, 1H).

1.4 Synthesis of (4R)-1-[(5-chloro-1H-1,2,4-triazol-1-yl)methyl]-4-(3,4,5-trifluoro-phenyl)pyrrolidin-2-one 7

1) To a cold solution (0° C.) of (4R)-1-(hydroxymethyl)-4-(3,4,5-trifluorophenyl)pyrrolidin-2-one 5 (4.7 g, 1 eq., 19.4 mmol) in $CH_2Cl_2$ (200 mL) is added oxalyl chloride (3.7 ml, 2 eq., 38 mmol). After stirring for 30 minutes at 0° C., the reaction mixture is evaporated in vacuum yielding (4R)-1-(chloromethyl)-4-(3,4,5-trifluorophenyl)pyrrolidin-2-one 6 which is dissolved in THF (100 ml) to afford Solution A.

2) To a cold solution (0° C.) of 5-chloro-1H-1,2,4-triazole (3.0 g, 1.5 eq., 29.1 mmol) in THF (100 ml) is added NaH 95% in mineral oil (0.9 g, 2 eq., 38.7 mmol). The reaction mixture is stirred during 30 minutes at 0° C. to afford Solution B.

3) Solution A is added to solution B at 0° C. and the reaction mixture is maintained under stirring overnight at room temperature. The mixture is quenched with water (100 ml) and extracted with AcOEt (2*100 mL). The combined organic extracts are washed with brine (100 ml), dried over $MgSO_4$ then concentrated under reduced pressure yielding 7 g of compound 7 as crude material. The crude residue is purified by chromatography on silicagel (eluent: $CH_2Cl_2$/MeOH/$NH_4OH$ 95/5/0.5 v/v/v) and recrystallized from $iPr_2O$/EtOH affording 1.6 g of (4R)-1-[(5-chloro-1H-1,2,4-triazol-1-yl)methyl]-4-(3,4,5-trifluorophenyl)pyrrolidin-2-one 7 as a white solid.

Yield: 25%.
LC-MS ($MH^+$): 331/333.
$^1$H NMR (DMSO) δ 8.12 (s, 1H), 7.32 (dd, $J_1$=9.2 Hz, $J_2$=6.9 Hz, 2H), 5.63 (d, J=1.5 Hz, 2H), 3.81 (t, J=8.6 Hz, 1H), 3.62 (t, J=8.4 Hz, 1H), 3.39 (m, 1H), 2.71 (dd, $J_1$=16.7 Hz, $J_2$=8.8 Hz, 1H), 2.54 (d, J=9.1 Hz, 1H).
$alpha_D$ (MeOH, 25° C.): +9.2.

Example 2

Synthesis of 1-{[(4R)-2-oxo-4-(3,4,5-trifluorophenyl)pyrrolidin-1-yl]-methyl}-1H-1,2,4-triazole-5-carbonitrile 8

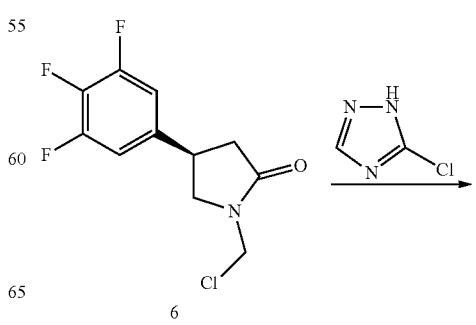

6

13

-continued

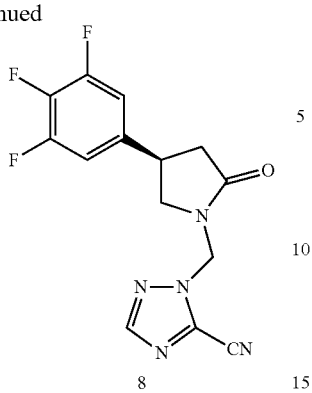
8

To a cold solution (0° C.) of 1H-1,2,4-triazole-5-carbonitrile (0.22 g, 1.5 eq., 2.3 mmol) in toluene (5 ml) is added NaH 95% in mineral oil (0.074 g, 2 eq., 3.1 mmol). After 1 hour stirring at 0° C., (4R)-1-(chloromethyl)-4-(3,4,5-trifluorophenyl)pyrrolidin-2-one 6 (0.41 g, 1 eq., 1.5 mmol) in toluene (1 ml) is added and the reaction mixture is maintained under stirring for 60 hours at room temperature. The mixture is quenched with water (20 ml) and extracted with AcOEt (2*10 ml). The combined organic extracts are washed with brine (50 ml), dried over MgSO₄ then concentrated under reduced pressure yielding 0.46 g of compound 8 as crude material. The crude residue is purified by reverse phase chromatography (Kromasil Eternity C18 column; gradient: water/CH₃CN/NH₄OH from 80/20/0.1 to 50/50/0.1 in 10 minutes) then by chiral chromatography (preparative Chiralpak IC 80*380 mm column; eluent: heptane/EtOH/diethylamine 50/50/0.1; isocratic flow, 200 ml/min, 30° C.) to afford 0.04 g of 1-{[(4R)-2-oxo-4-(3,4,5-trifluorophenyl)pyrrolidin-1-yl]methyl}-1H-1,2,4-triazole-5-carbonitrile 8 as a white solid.

Yield: 8%.

LC-MS (MH⁺): 322; LC-MS (MH⁻): 320.

¹H NMR (DMSO) δ 8.41 (s, 1H), 7.32 (m, 2H), 5.79 (m, 2H), 3.86 (t, J=8.6 Hz, 1H), 3.63 (quint, J=8.6 Hz, 1H), 3.45 (m, 1H), 2.71 (dd, J₁=16.8 Hz, J₂=8.6 Hz, 1H), 2.51 (m, 1H).

alpha$_D$ (MeOH, 25° C.): −7.2.

Example 3

Synthesis of (+)-3-{1-[(5-chloro-1H-1,2,4-triazol-1-yl)methyl]-5-oxopyrrolidin-3-yl}benzonitrile 14

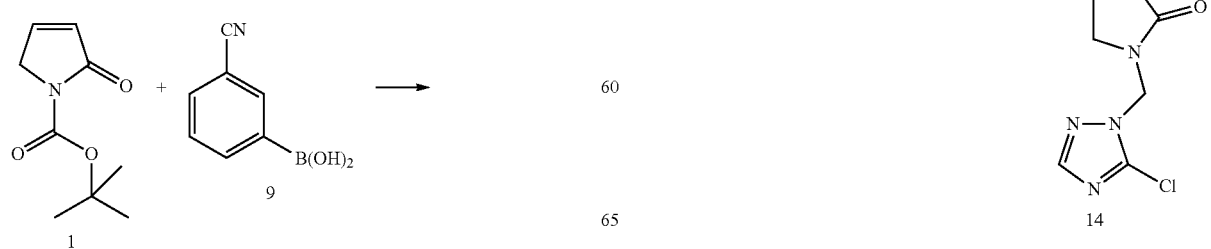

14

-continued

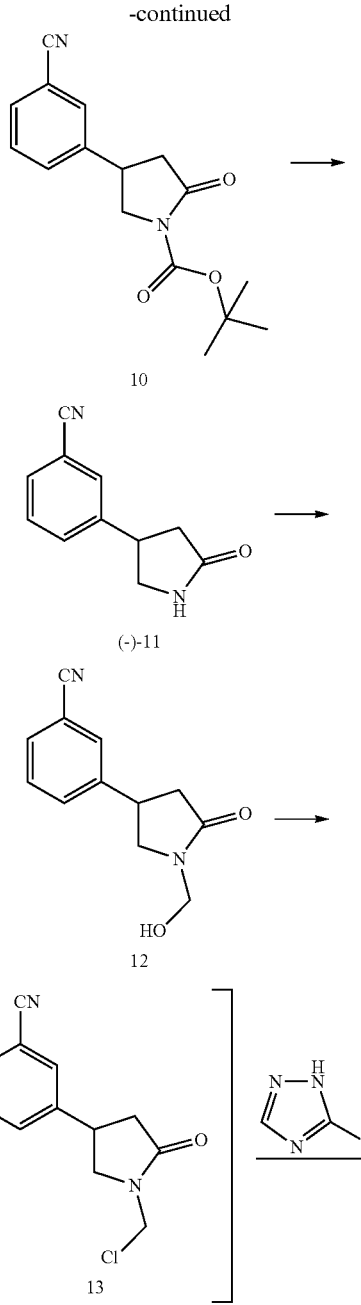

3.1 Synthesis of tert-butyl 4-(3-cyanophenyl)-2-oxopyrrolidine-1-carboxylate 10

To a solution of tert-butyl 2-oxo-2,5-dihydro-1H-pyrrole-1-carboxylate 1 (18.3 g, 1 eq., 100 mmol), (3-cyanophenyl) boronic acid 9 (29.4 g, 2 eq., 200 mmol) and potassium carbonate (0.69 g, 0.05 eq., 5 mmol) in dioxane/water (300 ml/5 ml) at reflux are successively added (R)-2,2'-bis(diphenyl-phosphino)-1,1'-binaphthyl (1.6 g, 0.025 eq., 2.5 mmol) and chloro(1,5-cyclooctadiene)rhodium(I) dimer (0.25 g, 0.005 eq., 0.5 mmol). The mixture is stirred at reflux for 8 h. Solvent are removed under reduced pressure, the residue is treated with water (150 ml) and extracted with iPrOAc (250 ml). Treatment of organic phase with a saturated aqueous solution of $NaHCO_3$ and extraction with iPrOAc affords, after concentration of the organic phase under vacuum, 33.9 g of tert-butyl 4-(3-cyanophenyl)-2-oxopyrrolidine-1-carboxylate 10 as a brown oil.

Yield: 100%.
LC-MS ($MH^+$): 287.

3.2 Synthesis of (−)-3-(5-oxopyrrolidin-3-yl)benzonitrile 11

Tert-butyl 4-(3-cyanophenyl)-2-oxopyrrolidine-1-carboxylate 10 (33.9 g, 1 eq., 100 mmol) in dichloromethane (100 ml) is added dropwise at 0° C. to a solution of TFA (31.2 ml, 4 eq., 400 mmol) in dichloromethane (100 ml). The mixture is stirred at room temperature for 2 h then quenched with water (100 ml). The organic phase is isolated and treated with a 5% aqueous solution of $NaHCO_3$ and concentrated under reduced pressure. The resulting brown solid is recrystallized from toluene yielding 7.8 g of (−)-3-(5-oxopyrrolidin-3-yl)benzonitrile 11 as a beige solid.

Yield: 42%.
LC-MS ($MH^+$): 187.
$^1$H NMR ($CDCl_3$) δ 7.52 (m, 4H), 6.13 (s, 1H), 3.84 (m, 1H), 3.74 (m, 1H), 3.42 (m, 1H), 2.79 (m, 1H), 2.46 (m, 1H).
alpha$_D$ (MeOH, 25° C.): −28.8.

3.3 Synthesis of 3-[1-(hydroxymethyl)-5-oxopyrrolidin-3-yl]benzonitrile 12

To a solution of (−)-3-(5-oxopyrrolidin-3-yl)benzonitrile 11 (10 g, 1 eq., 53.7 mmol) in THF (100 ml) are added potassium tert-butoxide (0.1 g, 0.025 eq., 1.34 mmol) and paraformaldehyde (2 g, 1.2 eq., 64.4 mmol) at room temperature. After 3 hours stirring, at 60° C., the mixture is quenched with brine (100 ml) and the aqueous phase is extracted with AcOEt (2*100 ml). The combined organic extracts are dried over $MgSO_4$ and concentrated under reduced pressure yielding 13.2 g of 3-[1-(hydroxymethyl)-5-oxopyrrolidin-3-yl]benzonitrile 12, which is used in the next step without any further purification.

LC-MS ($MH^+$): 217.

3.4 Synthesis of (+)-3-{1-[(5-chloro-1H-1,2,4-triazol-1-yl)methyl]-5-oxopyrrolidin-3-yl}benzonitrile 14

1) To a cold solution (0° C.) of 3-[1-(hydroxymethyl)-5-oxopyrrolidin-3-yl]benzonitrile 12 (5 g, 1 eq., 23.1 mmol) in dichloromethane (50 ml) is added oxalyl chloride (4.4 ml, 2 eq., 46.2 mmol). After stirring for 1 hour at 0° C., the reaction mixture is evaporated under vacuum yielding 3-[1-(chloromethyl)-5-oxopyrrolidin-3-yl]benzonitrile 13 which is dissolved in THF (100 ml) to afford Solution A.

2) To a cold solution (0° C.) of 5-chloro-1H-1,2,4-triazole (3.6 g, 1.5 eq., 34.7 mmol) in THF (100 ml) is added NaH 95% in mineral oil (1.1 g, 2 eq., 46.2 mmol). The reaction mixture is stirred during 30 minutes at −20° C. to afford Solution B.

3) Solution A is added to solution B at −20° C. and the reaction mixture is maintained under stirring for 1 hour at −20° C. The mixture is quenched with water (200 ml) and extracted with AcOEt (2*100 ml). The combined organic extracts are dried over $MgSO_4$ and concentrated under reduced pressure yielding 8.2 g of compound 14 as crude material. The crude residue is purified by reverse phase chromatography (LC/MS) (Kromasil Eternity C18 column; gradient: water/$CH_3CN$/$NH_4OH$ from 80/20/0.1 to 50/50/0.1 in 10 minutes) to afford (+)-3-{1-[(5-chloro-1H-1,2,4-triazol-1-yl)methyl]-5-oxopyrrolidin-3-yl}benzonitrile 14 (second eluted, 1.2 g) as a yellow oil.

Yield: 17%.
LC-MS ($MH^+$): 302/304.
$^1$H NMR (DMSO) δ 8.08 (s, 1H), 7.77 (s, 1H), 7.69 (d, J=7.6 Hz, 1H), 7.62 (m, 1H), 7.50 (t, J=7.7 Hz, 1H), 5.62 (s, 2H), 3.83 (t, J=8.7 Hz, 1H), 3.65 (quint, J=8.4 Hz, 1H), 3.40 (dd, $J_1$=9.0 Hz, $J_2$=7.9 Hz, 1H), 2.73 (dd, $J_1$=16.8 Hz, $J_2$=8.8 Hz, 1H), 2.51 (m, 1H).
alpha$_D$ (MeOH, 25° C.): +16.3.

Example 4

In Vivo Model for Assessing the Efficacy of a Test Compound in Learning and Memory Disorders (Novel Object Recognition Test; NOR)

Evaluation of promnesiant properties in the mouse model of 2-trial novel object recognition in a situation of scopolamine induced memory deficit: the two-trial object recognition paradigm, initially developed by Ennaceur and Delacour (1988) in the rat, can be considered as a model of episodic-like memory. This learning and memory paradigm is based on spontaneous exploratory activity of rodents and does not involve rule learning or reinforcement. The object recognition paradigm has been shown to be sensitive to the effects of ageing and cholinergic dysfunction (Scali et al, 1994; Bartolini et al, 1996). This model has been adapted to mice and validated using pharmacological agents (Bertaina-Anglade et al, 2003).

The purpose of the study is to evaluate the ability of test compounds to reverse the experimental deficit induced by scopolamine. The experiments was carried out using male C57BL/6J mice (Centre d'Elevage R. Janvier, B. P. 55, 53940 Le Genest-Saint-Isle, F.), weighing 20-35 g (10-14 weeks old) at their arrival that should meet inclusion criteria described in the experimental procedure. The animals were housed in groups of 4-9 in polypropylene cages (floor area=777 $cm^2$) under standard conditions: room temperature (22±2° C.), light/dark cycle (12 h/12 h), water and food (SAFE A04) ad libitum. The experimental arena is a square wooden box (40×40×40 cm) painted in dark blue, with 8*8 cm black painted squares under a clear plexiglass floor. The arena was placed in a dark room illuminated only by lamps giving a uniform dim light in the box (around 60 lux). The day before the test, mice were habituated to the environment for a maximum of 30 min. On experimental day, mice were submitted to two trials spaced by an intertrial interval of 60 min. During the first trial (acquisition trial, T1), mice were placed in the arena containing 2 identical objects and time required by each animal to complete 20 s of object exploration was determined with a cut-off time of 12 min. Exploration was considered to be directing the nose at a distance less than 2 cm from the object and/or touching the object. For the second trial (testing trial, T2), one of the objects presented in the first trial was replaced by an unknown object (novel object), mice were placed back in the arena for 5 min and exploration of each object together with locomotor activity was determined. A criterion of minimal level of object exploration was used in the study to exclude animals with naturally low levels of spontaneous exploration: only animals having a minimal level of object exploration of 3 s during the testing trial (Novel+Familiar≥3 s) were included in the study. The following parameters were measured: time required to achieve 20 s of object exploration on T1 (s), locomotor activity on T1 (number of crossed lines), time spent in active exploration of the familiar object on T2 (s), time spent in active exploration of the novel object on T2 (s), locomotor activity on T2 (number of crossed lines). The intraperitoneal route of administration was used to evaluate the promnesiant effects. Vehicle, or the compounds of formula I were administered 40 min before T1. Scopolamine was administered 30 min before T1.

Compounds of formula (I) according to the invention, tested according to the above protocol, displayed typically an activity of 50 mg/kg or less.

Example 5

In Vivo Model for Assessing the Efficacy of a Test Compound in Recognition Memory Deficit Induced by Acute Scopolamine Administration and Repeat Sub-Chronic Phencyclidine (PCP) in Novel Object Recognition Task in Rat The animals were housed in groups of 2-4 in polypropylene cages (floor area=1032 cm$^2$) under standard conditions: room temperature (22±2° C.), hygrometry (55±10%), light/dark cycle (12 h/12 h), air replacement (15-20 volumes/hour), water and food (SAFE A04) ad libitum. Rats were be allowed to acclimate to environmental conditions for at least 5 days prior to experimentation.

The experimental arena was a square wooden box (60×60×40 cm) painted dark blue, with 15×15 cm black painted squares under a clear plexiglass floor. The arena and the objects were cleaned using water between each trial in order to avoid odour trails left by rats. The arena was placed in a dark room illuminated only by halogen lamps oriented towards the ceiling and giving a uniform dim light in the box (around 60 lux). Animals to be tested were placed in the experimental room at least 30 min before testing. The day before the test, rats were allowed to freely explore the box for habituation.

On experimental day, rats were be submitted to two object exploration trials spaced by an inter-trial interval. During the first trial (acquisition trial), rats were placed in the arena containing 2 identical objects (familiar object) and time required to complete object exploration was determined within a limited time period (cut-off time). Exploration was define as directing the nose at a distance less than 2 cm from the object and/or touching the object. For the second trial (retention trial), one of the objects presented in the first trial was replaced by an unknown object (novel object), rats were placed back in the arena for 3 min and exploration of each object was measured. Locomotor activity was estimated during each trial by the number of line crossed per minutes.

An exclusion criterion was defined for animals with naturally low levels of spontaneous exploration, which explored too little during the retention trial. The following parameters were measured: time required to achieve object exploration on trial 1 (s), locomotor activity on trial 1 (number of crossed lines), time spent in active exploration of the familiar object on trial 2 (s), time spent in active exploration of the novel object on trial 2 (s), locomotor activity on trial 2 (number of crossed lines).

Two models of memory deficit were used: (A) acute ip injection of scopolamine hydrochloride 30 min before acquisition (trial 1) (0.3 mg/kg in saline, in a volume of 5 ml/kg) in male Sprague Dawley rats (220-300 g (6-7 weeks old) at the beginning of the experiments); and (B) repeat subchronic phencyclidine (5 mg/kg ip bid in a volume of 5 ml/kg) during 7 days followed by 7 days washout period before behavioral evaluation in male Long-Evans rats (160-220 g at the beginning of the experiments). Compound was administered per os 60 min before acquisition in a volume of 10 ml/kg in scopolamine model; and ip 40 min before acquisition in a volume of 5 ml/kg in sub-chronic PCP model. Vehicle was 1% methylcellulose (w/v) 0.1% Tween 80 (w/v), 0.1% silicon antifoam 1510 US (w/v) in water. The experimental parameters of the novel object recognition were adapted to each model and rat strain. These parameters are described in the table below.

| | Model | |
|---|---|---|
| Species/strain | acute scopolamine young male Sprague Dawley rats | sub-chronic PCP young male Long-Evans rats |
| Duration of habituation to the box | 3 min | 10 min |
| Duration of familiar object exploration during trial 1 (acquisition) | 15 s | 8 s |
| Cut off time for trial 1 | 4 min | 6 min |
| Inter-trial interval | 120 min | 30 min |
| Duration of trial 2 (retention) | 3 min | 3 min |
| Minimum exploration time during trial 2 | 5 s | 5 s |

Compounds of formula (I) according to the invention displayed typically an activity at 1 mg/kg or less in the scopolamine model and at 3 mg/kg or less in the sub-chronic PCP model.

Example 6

Y-Maze Test

A non transgenic model of amyloid-induced memory deficit is used comprising: a bolus intracerebral injection of the aggregated β25-35 amyloid peptide into the lateral ventricle of mouse. Such injection induced 7-12 days later Congo-red stained amyloid-like deposits in the hippocampus and cortex. It also induced a variety of memory deficits observed in the spontaneous alternation, the inhibitory avoidance, or the Morris water maze task.

The spontaneous alternation in rat and mice refers to the spontaneous behavior of rodent to alternate in a Y or T-maze. Spontaneous alternation behavior has been ascribed to the operation of a variety of mechanism, but regardless of his ethological function, it is evident that the animal must remember which arm it had entered on a previous occasion to enable it to alternate its choice on a following trial.

Therefore, spontaneous alternation has been embraced by behavioral pharmacologists as a quick and relatively simple test of memory devoid of fear, reward or re-enforcers.

A single unilateral intracerebral injection with 9 nmole aggregated β25-35 amyloid peptide was administered in the right lateral ventricle according to the technique of Maurice et al. (Brain Research. 1996; 706:181-193).

The Y-maze was a three equal-size-arm maze (39 cm long) made of white PVC. The arms were oriented at 60 angles from each other. The Y-maze test was done 7-12 days post-amyloid administration under moderate lighting condition (200 lux), with moderate background music and mild eucalyptus odor. Compounds were given intraperitoneally 40 min before Y-maze trial.

Young Male Swiss mice began the single trial at the end of one arm, and were allowed to freely explore the Y-maze during 8 min. Number and sequence of arm visits was recorded. Alternation was defined as "a consecutive entry in three different arms". The alternation percentage was computed with the following formula: "number of alternation" divided by "total number of arm visit" minus 2.

The test compounds displayed typically an activity at 10 mg/kg or less.

The invention claimed is:

1. A compound of formula (I)

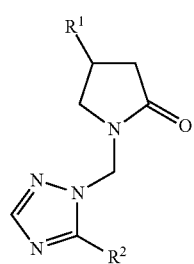

(I)

wherein
$R^1$ is either a 3,4,5-trifluorophenyl or a 3-cyanophenyl group;
$R^2$ is either cyano or chlorine;
or a tautomer, isomer or salt thereof.

2. The compound according to claim 1, wherein the $R^1$ group of formula (I) is in a 4R configuration.

3. The compound according to claim 2, wherein the $R^1$ group is a 3,4,5-trifluorophenyl moiety.

4. The compound according to claim 1, wherein the $R^1$ group of formula (I) is in a 4S configuration.

5. The compound according to claim 4, wherein the $R^1$ group is a 3,4,5-trifluorophenyl moiety.

6. The compound according to claim 1, wherein the $R^1$ group is a 3,4,5-trifluorophenyl moiety.

7. The compound according to claim 1 that is
 (4R)-1-[(5-chloro-1H-1,2,4-triazol-1-yl)methyl]-4-(3,4,5-trifluorophenyl)pyrrolidin-2-one;
 1-{[(4R)-2-oxo-4-(3,4,5-trifluorophenyl)pyrrolidin-1-yl]methyl}-1H-1,2,4-triazole-5-carbonitrile; or
 (+)-3-{1-[(5-chloro-1H-1,2,4-triazol-1-yl)methyl]-5-oxopyrrolidin-3-yl}benzonitrile.

8. A pharmaceutical composition containing a compound according to claim 1 together with a suitable pharmaceutically acceptable excipient.

9. A pharmaceutical composition containing a compound according to claim 2 together with a suitable pharmaceutically acceptable excipient.

10. A pharmaceutical composition containing a compound according to claim 7 together with a suitable pharmaceutically acceptable excipient.

11. A method of treating Alzheimer's disease in a human comprising administering to the human an effective amount of a compound according to claim 1.

12. A method of treating Alzheimer's disease in a human comprising administering to the human an effective amount of a compound according to claim 2.

13. A method of treating Alzheimer's disease in a human comprising administering to the human an effective amount of a compound according to claim 4.

14. A method of treating Alzheimer's disease in a human comprising administering to the human an effective amount of a compound according to claim 6.

15. A method of treating Alzheimer's disease in a human comprising administering to the human an effective amount of a compound according to claim 7.

16. A method of treating Alzheimer's disease in a human comprising administering to the human an effective amount of a compound according to claim 3.

17. A method of treating Alzheimer's disease in a human comprising administering to the human an effective amount of a compound according to claim 5.

* * * * *